(12) United States Patent
Seto et al.

(10) Patent No.: US 7,192,763 B2
(45) Date of Patent: Mar. 20, 2007

(54) STREPTOMYCES ANULATUS MICROORGANISM AND A PROCESS FOR PRODUCING THE SUBSTANCE GM-95

(75) Inventors: Haruo Seto, Hachioji (JP); Kazuo Shin-Ya, Tokyo (JP); Konstanty Wierzba, Sayama (JP)

(73) Assignee: Sosei Co., Ltd. (JP)

( * ) Notice: Subject to any disclaimer, the term of this patent is extended or adjusted under 35 U.S.C. 154(b) by 394 days.

(21) Appl. No.: 10/401,589

(22) Filed: Mar. 31, 2003

(65) Prior Publication Data

US 2003/0191165 A1 Oct. 9, 2003

Related U.S. Application Data

(62) Division of application No. 09/806,475, filed on Apr. 9, 2001, now Pat. No. 6,613,759.

(51) Int. Cl.
C12N 1/20 (2006.01)
C12P 17/18 (2006.01)

(52) U.S. Cl. .................... 435/253.5; 435/119
(58) Field of Classification Search .................... None
See application file for complete search history.

(56) References Cited

U.S. PATENT DOCUMENTS 3,325,359 A * 6/1967 De Somer et al. .......... 424/115
5,567,709 A 10/1996 Skotnicki et al.

FOREIGN PATENT DOCUMENTS

| EP | 0269322 A1 | 6/1988 |
| EP | 849267 | 6/1998 |
| JP | 11-180997 | 6/1999 |

OTHER PUBLICATIONS http://www.atcc.org/common/catalog/wordSearch/results.cfm, accessed Jul. 5, 2006.*
European Search Report, Jan. 2000.

* cited by examiner

*Primary Examiner*—Irene Marx
(74) *Attorney, Agent, or Firm*—Rader, Fishman & Grauer PLLC

(57) ABSTRACT

A compound which has the following formula (1),

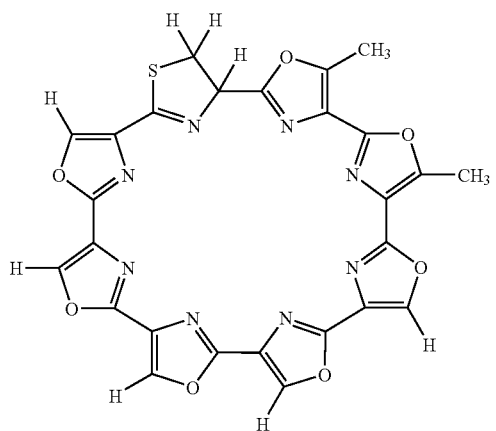

a process for its production, a pharmaceutical composition comprising the compound as an active ingredient, a method of treating tumor which comprises administering the compound, use of the compound as a medicine, and a microorganism capable of producing the compound. The compound of the present invention is a novel compound which has antitumor action and is useful as a medicine.

8 Claims, 4 Drawing Sheets

STREPTOMYCES ANULATUS MICROORGANISM AND A PROCESS FOR PRODUCING THE SUBSTANCE GM-95

RELATED APPLICATION

This application is a divisional application of application Ser. No. 09/806,475, filed on Apr. 9, 2001 now U.S. Pat No. 6,613,759.

TECHNICAL FIELD

The present invention relates to a novel compound which has antitumor effects and is useful as a medicine, to a process for producing the same, and to microorganisms producing the substance.

BACKGROUND ART

Known examples of a macrolide having two or more oxazole rings include Ulapualide A and B (Journal of American Chemical Society, 108, 846–847, 1986) which are extracted from nudibranches and have antitumor activities, and Kabiramide C (Journal of American Chemical Society, 108, 847–849, 1986) which is also extracted from nudibranches and has antifungal effects.

An object of the present invention is to obtain, using a microorganism, a novel compound which has antitumor effects and is useful as a medicine, a process for producing the same, and microorganisms capable of producing the novel compound which has antitumor effects.

DISCLOSURE OF INVENTION

The inventors of the present invention have studied various compounds produced by microorganisms and found that a substance having antitumor activities was produced in a culture broth of 3533-SV4 strain which belongs to the genus *Streptomyces*. Subsequently, the inventors succeeded in isolating the active substance, determined its physicochemical properties and structure, and verified its antitumor effects, to thereby accomplish the present invention.

The present invention provides a compound of the following formula (1).

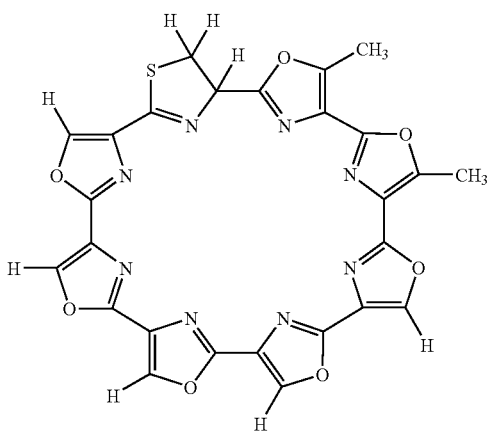

(1)

The above compound is hereinafter referred to as "Substance GM-95".

The present invention further provides a process for producing Substance GM-95 which comprises cultivating a microorganism belonging to the genus *Streptomyces* and capable of producing Substance GM-95 in a culture medium, and isolating the substance from the resultant culture broth.

The present invention further provides a medicine and an antitumor agent comprising Substance GM-95 as an active ingredient.

The present invention further provides a pharmaceutical composition comprising Substance GM-95 and a pharmaceutically acceptable carrier therefor.

The present invention further provides a method of treating tumors which comprises administering an effective amount of Substance GM-95 to a patients.

The present invention further provides a use of Substance GM-95 for a medicine.

Furthermore, the present invention provides microorganisms capable of producing Substance GM-95, more specifically the microorganisms belonging to the genus *Streptomyces*.

BEST MODE FOR CARRYING OUT THE INVENTION

Physicochemical properties of Substance GM-95 represented by the above formula (1) are as follows.

1) Molecular formula: When measured by high-resolution fast atomic bombardment mass spectrometry, the measured value of (M+H)$^+$ of 583.0790 is shown, and the molecular formula which corresponds to the value is $C_{26}H_{15}N_8O_7S$.

2) Molecular weight: When measured by fast atomic bombardment mass spectrometry, the measured value of 582.0712 is shown.

3) Melting point: 138–143° C. (decomposition)

4) Specific rotation: $[\alpha]_D^{20} = -9.38°$, determined at the concentration of C=0.129 g/100 ml (methanol).

Figure 1:
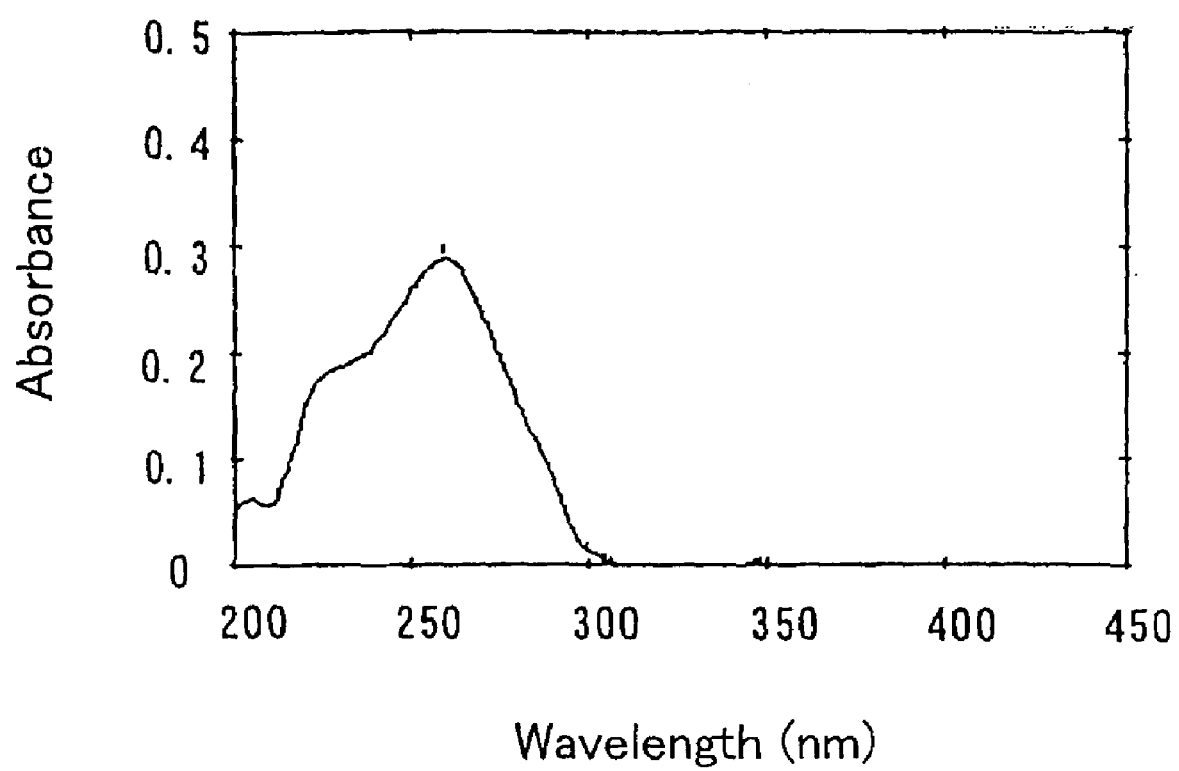
FIG. 1 shows an ultraviolet absorption spectrum of the present compound as obtained in EXAMPLES.

5) Ultraviolet absorption spectrum: shown in FIG. 1.

The measurement was conducted in methanol (in a 7.39 µM solution). The maximum absorption was at the wavelength of 259.5 nm and the absorbance at the wavelength was 0.288. A molar absorption coefficient (ε) was 38982.

Figure 2:
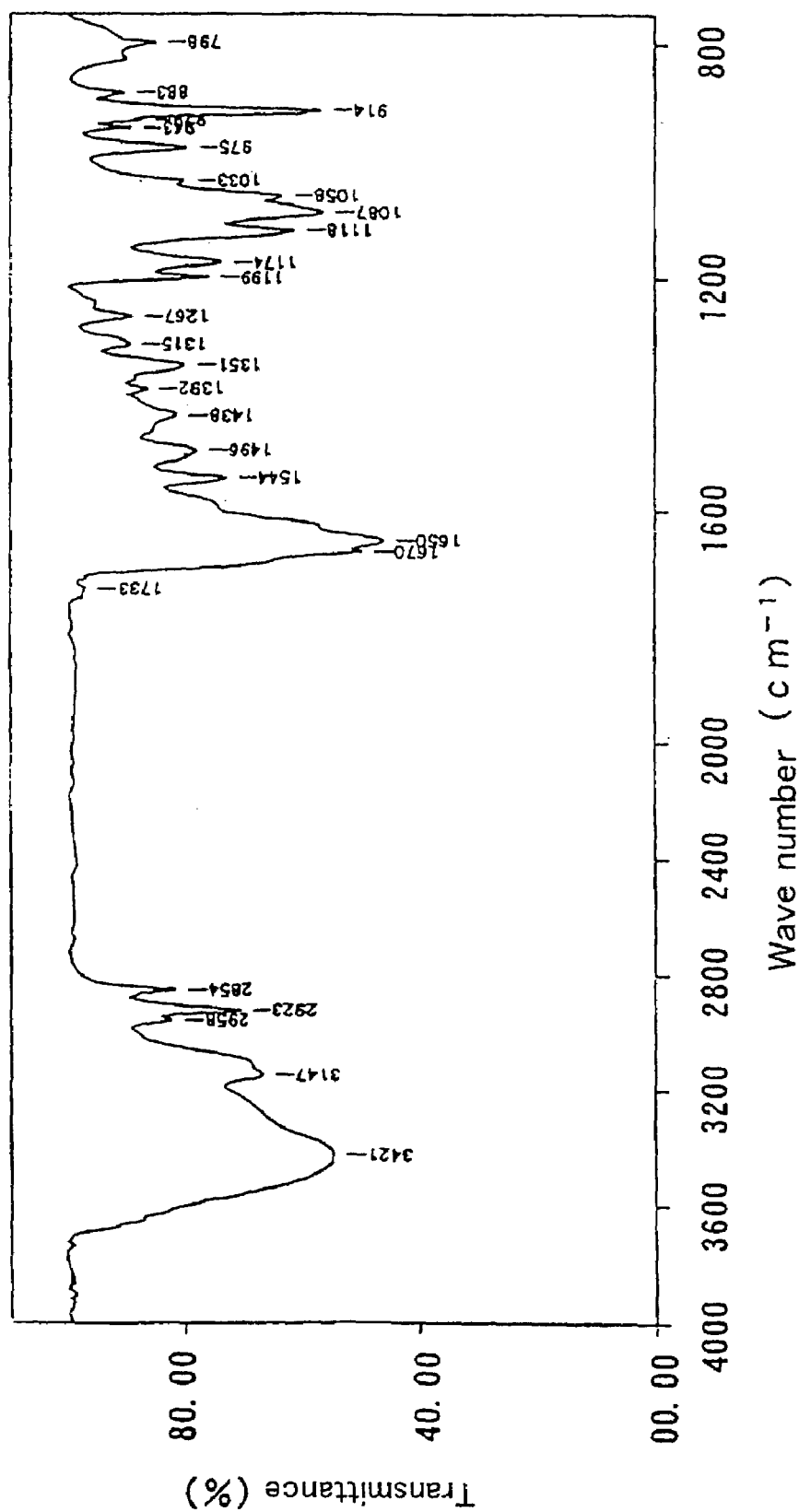
FIG. 2 shows an infrared absorption spectrum of the present compound as obtained in EXAMPLES.

6) Infrared absorption spectrum (FT-IR): shown in FIG. 2. νmax (cm$^{-1}$):

3421, 3147, 2958, 2923, 2854, 1733, 1670, 1650, 1544, 1496, 1438, 1392, 1351, 1315, 1267, 1199, 1174, 1118, 1087, 1058, 1033, 975, 943, 929, 914, 883, 798

7) Solubilities in solvents

Insoluble in water and in acetone.

Soluble in a mixture of chloroform:methanol=1:1

8) Color of the substance: white yellowish powders

9) Nuclear magnetic resonance spectrum

Figure 3:
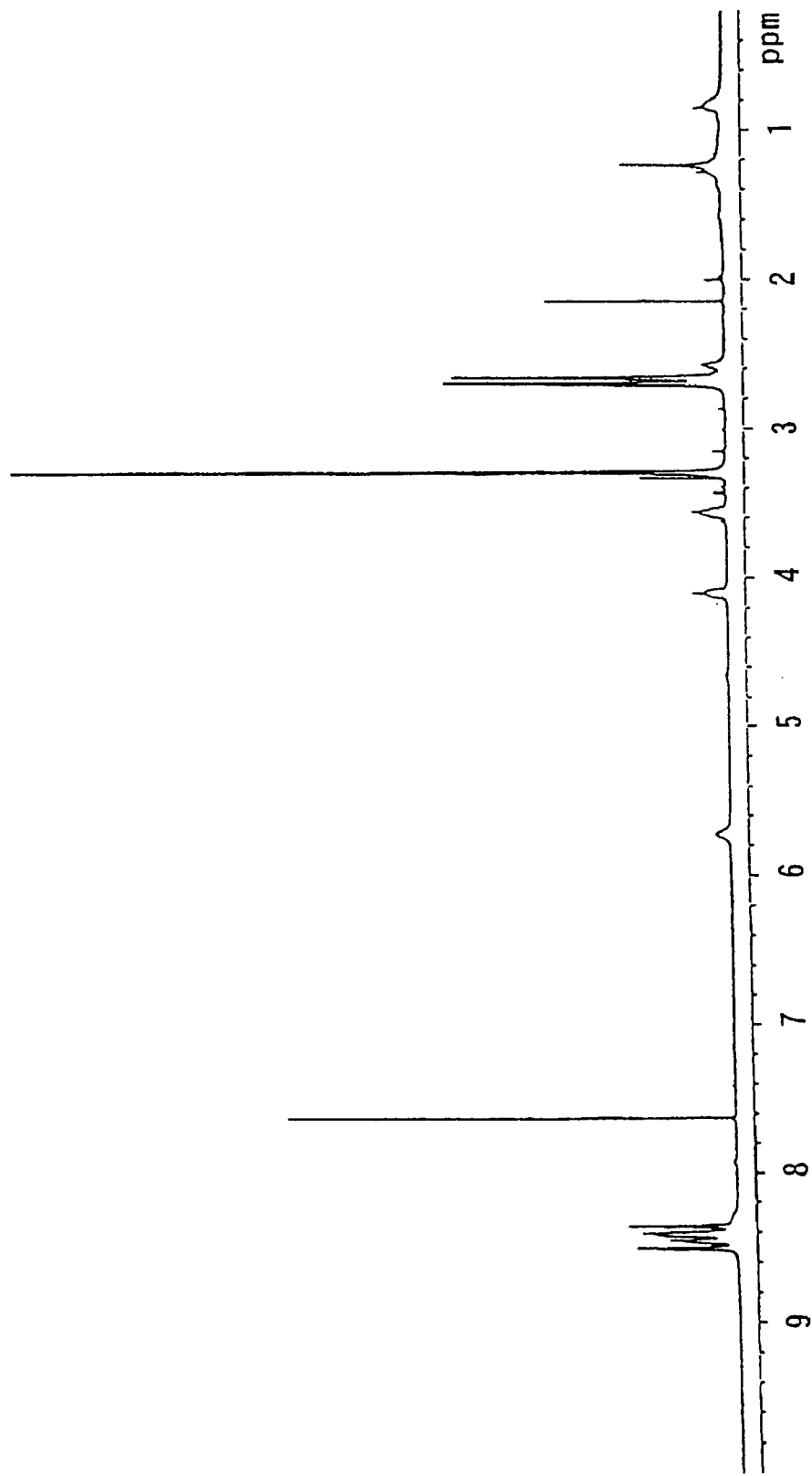
FIG. 3 shows a $^1$H-NMR spectrum of the present compound as obtained in EXAMPLES.
Figure 4:
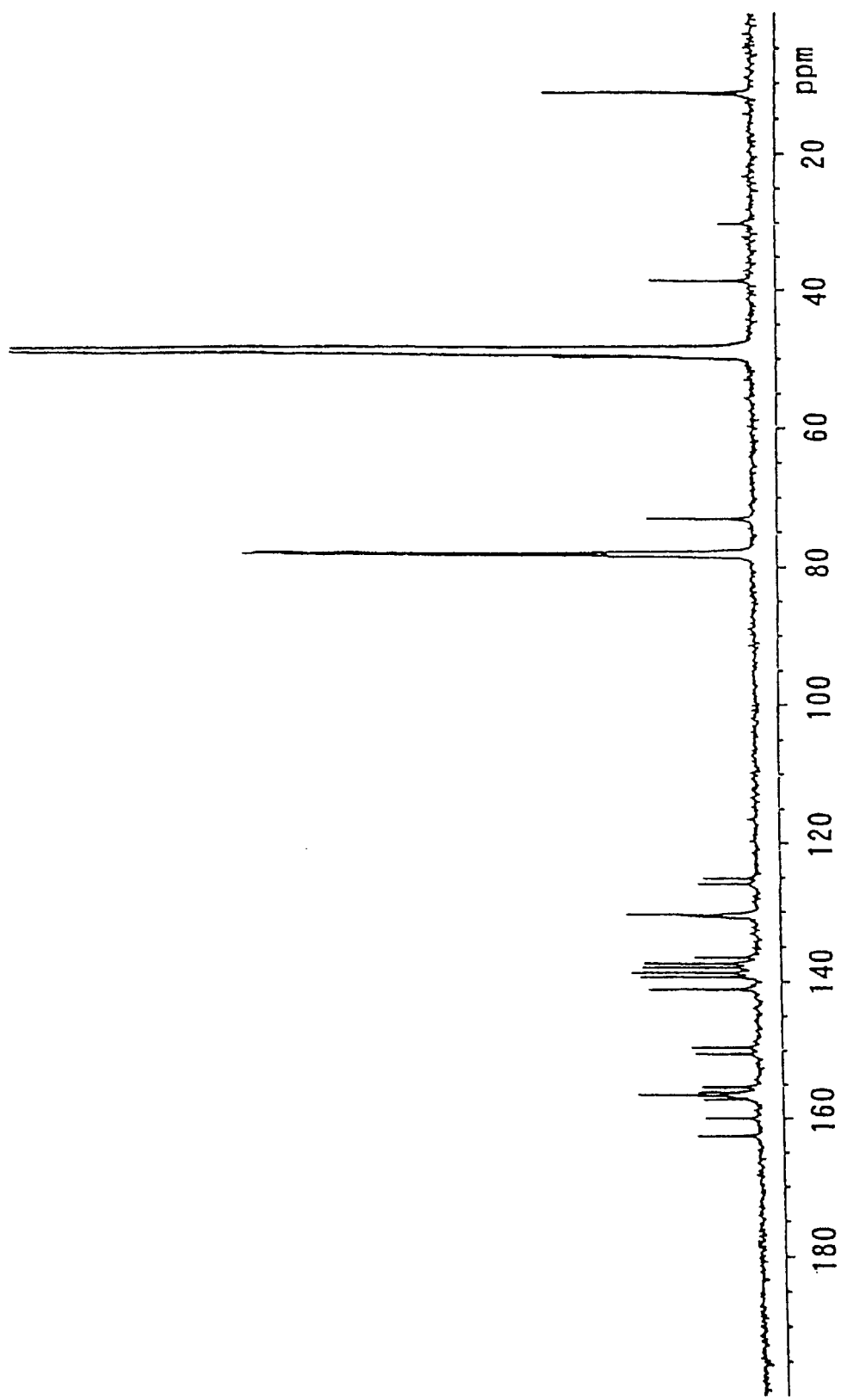
FIG. 4 shows a $^{13}$C-NMR spectrum of the present compound as obtained in EXAMPLES.

The chemical shifts of the 500 MHz $^1$H-NMR spectrum (FIG. 3) and the 125 MHz $^{13}$C-NMR spectrum (FIG. 4)

measured in the solution of a mixture of deuterated chloroform:deuterated methanol=1:1 at 25° C. are shown below.

TABLE 1

(1)

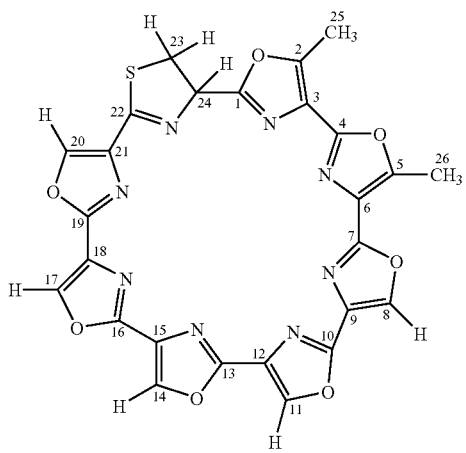

| Position of carbon | $^{13}$C-NMR | $^1$H-NMR |
|---|---|---|
| 1 | 162.5 | |
| 2 | 150.5 | |
| 3 | 125.1 | |
| 4 | 155.4 | |
| 5 | 149.6 | |
| 6 | 126.0 | |
| 7 | 157.3 | |
| 8 | 137.8 | 8.17(s, 1H) |
| 9 | 130.4 | |
| 10 | 156.8 | |
| 11 | 138.8 | 8.24(s, 1H) |
| 12 | 130.7 | |
| 13 | 156.2 | |
| 14 | 141.2 | 8.00(s, 1H) |
| 15 | 136.7 | |
| 16 | 156.6 | |
| 17 | 139.4 | 8.28(s, 1H) |
| 18 | 130.9 | |
| 19 | 156.6 | |
| 20 | 138.1 | 8.18(s, 1H) |
| 21 | 130.4 | |
| 22 | 160.0 | |
| 23 | 38.7 | 3.8(m, 1H), 3.46(m, 1H) |
| 24 | 73.2 | 6.19(br s, 1H) |
| 25 | 11.5 | 2.47(s, 3H) |
| 26 | 11.5 | 2.64(s, 3H) |

(10) Retention time (Rt) in high performance liquid chromatography (HPLC):

A peak was detected at a time of 6.1 min. upon analysis under the following conditions.

Analytical Conditions:

Column: PEGASIL ODS (4.6 mm I.D.×250 mm, Senshu Scientific Co.)

Mobile phase: acetonitrile/trifluoroacetic acid/water (70:0.1:30, v/v/v)

Flow rate: 1 ml/min.

Detection: 254 nm

Substance GM-95 of the present invention can be produced by cultivating a strain of microorganism capable of producing the substance of the invention (hereinafter referred to as a substance GM-95-producing microorganism) under appropriate conditions, typically under the following conditions. The present invention also encompasses the substance GM-95-producing microorganism.

Examples of the substance GM-95-producing microorganism include strains of microorganism belonging to the genus *Streptomyces*. The present invention also encompasses Substance GM-95 which can be obtained by cultivating a microorganism of the genus *Streptomyces* and recovering the culture broth.

Example of the strains of microorganism belonging to the genus *Streptomyces* are *Streptomyces anulatus* 3533-SV4 strain and mutants thereof. The *Streptomyces anulatus* 3533-SV4 strain is a strain of microorganism which belongs to the genus *Streptomyces* and which was newly isolated by the inventors from soil in Tensui-machi, Tamana-gun, Kumamoto-ken, Japan and has been deposited with National Institute of Bioscience and Human-Technology Agency of Industrial Science and Technology (1–3 Higashi 1 chome, Tsukuba-shi, Ibaraki-ken, Japan) on Aug. 12, 1998 under the designation of microorganism: *Streptomyces anulatus* 3533-SV4(GM95) (Identification reference given by the DEPOSITOR) and the accession number of FERM BP-6460.

Identification of the *Streptomyces anulatus* 3533-SV4 and investigation of its microbiological characteristics were conducted according to the method of International *Streptomyces* Project (ISP). The microbiological characteristics of *Streptomyces anulatus* 3533-SV4 strain are as follows.

a) Morphological Characteristics

The strain was grown on ISP (International *Streptomyces* Project) media No. 2, No. 3, No. 4 and No. 5 at 27° C. for 14 days. The results are as follows:

1) Branching of sporulating hyphae: Simple branching
2) Form of sporulation: Spirals, spore form being cylindrical shape.
3) Number of spores: 10 to 50 or more
4) Surface of spores: Smooth
5) Size of spore: 0.3–0.5×0.7–1.0 μm
6) Presence of flagellate: Not present
7) Presence of sporangia: Not present
8) Attachment site of sporophores: Aerial mycelium
9) Possession of sclerotium-forming ability: No possession b) Cultural Characteristics on Various Media Cultural characteristics of the strain on various media are shown in Table 2. Color tones related to the properties of the media shown in Table 2 are indicated according to The Color Harmony Manual (1958 edition) published by Container Corporation of America.

TABLE 2

| Medium | Color tone of aerial mycelium | Color tone of substrate mycelium | Soluble pigment |
|---|---|---|---|
| Sucrose nitrate agar | Yellow color series | Pale yellow | None |
| Glucose asparagine agar | Yellow color series | Pale yellowish brown/Bright yellow | None |
| Glycerin asparagine agar | Yellow color series | Pale yellow | None |
| Starch inorganic salt agar | Yellow color series | Bright yellowish brown/Pale yellowish brown | None |
| Tyrosine agar | Yellow color series | Bright yellowish brown | Brownish white |
| Nutrient agar | Yellow color series | Pale yellow | None |
| Yeast malt agar | Yellow color series | Pale yellowish brown | None |
| Oatmeal agar | Yellow color series | Pale yellow/Bright yellowish brown | None | c) Physiological Characteristics

1) Temperature range for growth: 20–32° C. Optimum Temperature: 20–30° C.
2) Liquefaction of gelatin:+
3) Hydrolysis of starch:+
4) Coagulation and peptonization of skimmed milk:+
5) Production of melanoid pigments:

Tyrosine agar medium:–

Peptone yeast iron agar medium:–

Tryptone yeast broth medium:+
6) Reduction of nitrates:+
7) Assimilation of Carbon Sources (Pridham·Gottlieb agar medium, (ISP No. 9))

| | |
|---|---|
| L-arabinose | + |
| D-xylose | + |
| D-glucose | + |
| D-fructose | + |
| Sucrose | + |
| Inositol | + |
| L-rhamnose | + |
| Raffinose | + |
| D-mannitol | + | d) Chemotaxonomy

The acid hydrolysis products of the whole cells were analyzed by thin-layer chromatography described in The Society for Actinomycetes Japan (ed.), [Experimental Method for Identifying Actinomycetes-6-2-70, 1985]. As a result, LL-form of diaminopimelic acid was detected.

The substrate mycelium of this strain are not fragmented. The aerial mycelium forms a long main axis and a spiral spore chain which consists of 10–50 or more spores and has 4–9 rotations on tips of each mycelia irregularly branched from the axis. The spores have non-motility, a columnar or a elliptical shape, the width of 0.3–0.5, the length of 0.7–1.0 μm and smooth surface. A sclerotium, sporangias, and other specific forms are not observed. The chemotype of cell wall is type (I). Cultivation properties are shown in Table 2. A color tone of the aerial mycelium is yellow color series. The color tone of the substrate mycelium is unclear and not affected by the change of pH. No soluble pigment is observed overall. Physiological properties are as described in the above item c). This strain is mesophilic. According to the morphological properties and the chemotype of the cell wall of this strain, the strain is determined to belong to the genus Streptomyces (hereinafter abbreviated to "S.").

Based on the above properties, species of the genus S. described in [Approved Lists of Bacterial Names, 1980] and the subsequent lists of available bacterial names were searched and related species were selected. Compared to diagnostic properties of S. spheroides, the properties of the strain of the invention and S. spheroides are almost the same and distinct only in assimilation of carbon sources.

Accordingly, the strain of the invention is a new strain which closely resembles S. spheroides. However, S. spheroides is defined as a synonym of S. anulatus by Williams et al. in Bergey's Manual of Systematic Bacteriology vol. 4. Consequently, the 3533-SV4 strain of the invention is identified as a strain belonging to S. anulatus and named as Streptomyces anulatus 3533-SV4 strain.

The following are the comparisons between the strain and related species.

TABLE 3

| | | Strain 3533-SV4 | Streptomyces spheroides |
|---|---|---|---|
| Form of spore chain | Spirals | + | + |
| Spore surface | Smooth | + | + |
| Color tone of aerial mycelium | Yellow color | + | + |
| Color tone of Substrate mycelium | Unclear color | + | + |
| PH sensibility | | – | – |
| Production of soluble pigment | | – | – |
| Production of melanin pigment | | – | – |
| Hydrolysis of starch | | + | + |
| Reduction of nitrates | | + | + |
| Growth temperature | 10° C. | – | – |
| | 45° C. | – | – |
| Assimilation of carbon | | | |
| Arabinose | | + | – |
| Xylose | | + | + |
| Inositol | | + | – |
| Mannitol | | + | + |
| Rhamnose | | + | + |
| Raffinose | | + | – |
| Sucrose | | + | + |
| Fructose | | + | + |

Substance GM-95 of the present invention can be produced by cultivating various substance GM-95-producing microorganisms, for example, belonging to genus Streptomyces, such as 3533-SV4 strain or a mutant thereof having the above microbiological characteristics, in a suitable medium, separating a crude extract containing the substance of the invention from a culture broth, and isolating and purifying Substance GM-95 from the crude extract. The culture broth contains culture filtrate and solid cellular fractions.

Culture of the microorganism of the invention is carried out in accordance with the conventional cultural procedure and generally, is preferably carried out aerobically in a fluid medium by a shake culture process or an aerobic spinner culture process and like process. As the culture medium which can be used, any medium can be employed that contains nutrient sources which the substance GM-95-producing microorganism can utilize and a variety of synthetic media and natural media can be utilized. The carbon source added to the medium includes glucose, sucrose, fructose, glycerin, dextrin, starch, molasses, corn steep liquor, and organic acids, etc, and those sources can be used alone or in combination. The nitrogen source includes organic nitrogenous substances such as Pharma media, peptone, meat extract, yeast extract, soybean meal, casein, amino acids, urea, etc. and inorganic nitrogenous substances such as sodium nitrate, ammonium sulfate, etc. Those substances may also be used alone or in combination. Where necessary, the medium may be supplemented with sodium salts, potassium salts, magnesium salts, phosphates, and heavy metal salts suitably.

When copious foaming is encountered in the course of culture, an antifoaming agent may be added to the medium. Examples of antifoaming agents are vegetable oils, e.g. soybean oil, linseed oil, etc., higher alcohols, e.g. octadecanol, tetradecanol, heptadecanol, etc., and various silicon compounds.

The pH value of the medium is preferably controlled around neutrality. The cultivation temperature should be maintained within the range suitable for growth of the substance GM-95-producing microorganism, generally 20–32° C., preferably around 25–30° C. The cultivation time is preferably 2–6 days for both shake culture process and aerobic spinner culture process.

The various incubation conditions explained above can be suitably modified according to the kind and characteristics of the microorganism used, external conditions and the like, and optimum conditions may be selected from and controlled within the above ranges.

Separation of a crude extract containing Substance GM-95 from the culture broth can be achieved according to the conventional procedure for isolating fermentation products. For example, the routine procedure such as solvent extraction, chromatography, crystallization, etc. can be used singly or in a suitable sequence and combination.

More specifically, the following method may be used. Since Substance GM-95 produced in the course of culture exists mostly in culture filtrate and cell pellets, the culture broth is filtered or centrifuged in a conventional manner to separate the solid cellular fraction from the culture filtrate. Then Substance GM-95 is eluted from the solid cellular fraction which contains Substance GM-95 using a solvent such as methanol, acetone, etc. Subsequently, the solvent is distilled off under reduced pressure to provide a crude concentrate containing Substance GM-95. To the crude concentrate is added ethyl acetate, chloroform, butanol or like water-insoluble organic solvent to transfer Substance GM-95 into the organic solvent layer, and then the solvent layer is dehydrated by adding mirabilite. Subsequently, the solvent is distilled away under reduced pressure to provide the crude extract containing Substance GM-95. Further, Substance GM-95 contained in the culture filtrate may also be transferred into the organic solvent layer as stated above to provide the crude extract. Optionally, the steps such as adjusting pH with sodium hydroxide or hydrochloric acid, raising extract efficiency and preventing emulsion production by adding industrial salt, etc. may be taken.

Substance GM-95 can be isolated and purified from the above crude extract by the conventional procedure for the isolation and purification of low molecular weight lipophilic substances, such as adsorption chromatography using activated carbon, silica gel, alumina, nonionic macroporous adsorbent resins or like absorbents, reversed phase chromatography using ODS-bonded silica gel or the like. Among those techniques, silica gel chromatography using as eluent chloroform or a mixture of chloroform/methyl acetate, chloroform/methanol, chloroform/acetone, benzene/acetone, etc., and reversed phase chromatography using as eluent acetonitrile or a mixture of methanol/0.05% of trifluoroacetic acid or 10 mM of monopotassium phosphate etc. are particularly useful. Moreover, when further purification is needed, the above chromatographic procedure can be repeated or carried out in combination with column chromatography using Sephadex LH-20 (Pharmacia) and chloroform, methanol, etc. as eluent or like techniques. By the above procedure, Substance GM-95 of a high purity grade can be obtained.

For identification of Substance GM-95 during the purification procedure, the detection by thin-layer chromatography and by high performance liquid chromatography can be advantageously carried out in combination.

Substance GM-95 of the invention has antitumor activities, and its efficacy as an antitumor agent has been confirmed.

To use Substance GM-95 as purified as above in the form of a pharmaceutical composition, it is processed into a pharmaceutically suitable dosage form according to the intended application. The dosage form includes oral dosage forms such as tablets, capsules, powders, granules, fine granules, liquids and solutions, pills, emulsions, suspensions, etc., and parenteral dosage forms such as injections, suppositories, ointments, plasters, cataplasm, aerosols, ophthalmic solutions, etc. Those dosage forms can be manufactured by a known to and commonly used procedures by a person skilled in the art.

In manufacturing of solid preparations for oral administration, a excipient and optionally a binders, a disintegrator, a lubricants, a coloring agents, a corrigent, an aroma corrigent, etc. are added, to the active ingredient of the invention, and tablets, capsules, powders, granules, fine granules, etc. can be manufactured in the routine manner. Examples of the excipient includes lactose, sucrose, starch, talc, magnesium stearate, crystalline cellulose, methylcellulose, carboxymethylcellulose, glycerin, sodium alginate, acacia, etc., and of the binder includes polyvinyl alcohol, polyvinyl ether, ethyl cellulose, acacia, shellac, white sugar, etc., and of the disintegrator includes dried starch, sodium alginate, agar powder, sodium hydrogencarbonate, calcium carbonate, sodium lauryl sulfate, glyceryl monostearate, lactose, etc., and of the lubricant includes magnesium stearate, talc, etc., and of the corrigent includes white sugar, bitter orange peel, citric acid, tartaric acid, etc. The coloring agent, the aroma corrigent and other additives which are known in the art may be used. Where necessary, such tablets can be further processed into coated tablets by forming an ordinary coating film by a known method, for example sugar-coated tablets, gelatin-coated tablets, enteric coated tablets, film-coated tablets, etc., and can be double-layer tablets, multiple-layer tablets, etc.

In manufacturing of liquid preparations for oral administration, a corrigent, a buffer, a stabilizer, an aroma corrigent, etc. are added, to the active ingredient of the invention, and solutions, syrups and elixirs can be manufactured in the routine manner. Usable corrigents are mentioned above. The buffer that can be used includes sodium citrate, etc. and the stabilizer includes gum tragacanth, acacia, and gelatin, etc.

In manufacturing of injections, a diluent, a pH control agent, a buffer, a stabilizer, an isotonic agent, a local anesthetic, etc. are added, to the active ingredient of the invention, and injections for intravenous, intramuscular, subcutaneous, intradermal, or intraperitoneal administration can be manufactured in the routine manner. The diluent that can be used includes water, ethyl alcohol, macrogols, propylene glycol, ethoxylated isostearyl alcohol, polyoxylated isostearyl alcohol, polyoxyethylene sorbitan fatty acid esters, etc. The pH control agent or the buffer includes sodium citrate, sodium acetate, and sodium phosphate. The stabilizer includes sodium pyrosulfite, ethylenediaminetetracetic acid, thioglycolic acid, and thiolactic acid, among other substances. The isotonic agent that can be used includes sodium chloride, glucose, etc., and the local anesthetic includes procaine hydrochloride, lidocaine hydrochloride, etc.

In manufacturing of suppositories, a suppository base, optionally a surfactant, etc., are added, to the active ingredient of the invention, suppositories can be manufactured in the routine manner. The base that can be used includes oleaginous bases such as macrogols, lanolin, cacao butter, fatty acid triglycerides, Witepsol.RTM. (Dynamit Nobel), etc.

In manufacturing of ointments, a base, a stabilizer, a moistening agent, a preservative, etc., are added, as required, to the active ingredient of the invention and the mixture and formulation are processed in the routine manner. The base includes liquid paraffin, white soft paraffine, white beeswax, octyldodecyl alcohol, and paraffin; and the preservative includes methyl p-hydroxybenzoate, ethyl p-hydroxybenzoate, propyl p-hydroxybenzoate, etc.

In manufacturing of cataplasms, they can be manufactured by coating a conventional support with said ointment, cream, gel, paste, etc., in a routine manner. The supports include woven or nonwoven fabrics of cotton, spun rayon yarn or chemical fiber, films of flexible polyvinyl chloride, polyethylene, polyurethane, etc., and foamed sheets of such materials.

Where necessary, the dosage forms described above may be supplemented with other additives such as colorants, preservatives, perfumes, flavors, sweeteners, etc. or other medicinally active ingredients.

The proportion of the substance of the invention in the pharmaceutical composition of the invention is not so critical and can be selected liberally from a broad range but, generally speaking, is preferably 1–70 weight % in the pharmaceutical composition.

There is no limitation on the mode of administration of the pharmaceutical composition of the invention manufactured by the above methods. Thus, a suitable mode can be selected according to the particular dosage form, the patient's age, sex, and other factors, and the severity of disease. Preparations in injection form may be administered intravenously, intramuscularly, subcutaneously, intradermally or intraperitonally. If necessary, the injections can be administered intravenously in admixture with an ordinary infusion liquids such as a glucose solution or an amino acid solution. Solid preparations such as tablets, pills, granules, capsules, etc. and liquid preparations for oral administration of the invention may be administered orally or enterally. Suppositories may be administered into the rectum.

The amount of the active compound of the invention which is to be formulated in each dosage unit of the above forms cannot be defined in general terms, for it depends on the clinical condition of the patient and the dosage form. Generally, the amount in each unit dosage form is preferably about 1–1000 mg for oral preparations, about 0.1–500 mg for injections, and about 5–1000 mg for suppositories.

The dosage per day of the active compound in any of the above dosage forms can be suitably selected according to the patient's condition, body weight, age, sex, and other conditions. Usually, the dosage per day for an adult patient may be about 0.1–1000 mg/kg and preferably about 1–100 mg/kg. This dosage can be administered once or in about 2–4 divided doses per day.

The tumors which can be treated by administering the preparations containing Substance GM-95 of the invention is not limited to and include a solid malignant tumor such as head and neck cancer, esophageal cancer, gastric cancer, colon cancer, rectal cancer, liver cancer, gallbladder cancer or cholangioma, pancreatic cancer, renal cancer, pulmonary carcinoma, breast cancer, ovarian cancer, bladder cancer, prostate cancer, testicular tumor, osteosarcoma, soft tissue tumors, cervical cancer, skin cancer, brain tumors, etc., a malignant lymphoma and leukemia, preferably a malignant solid tumor.

EXAMPLES

The following working examples and test examples illustrate the invention in further detail.

Example 1

Preparation for Substance GM-95

(a) Culture Process

A test tube (50 ml) was charged with 15 ml of a pre-culture medium (pH 7.2) containing 1.0% soluble starch, 1.0% polypeptone, 1.0% molasses and 1.0% beef extract, and after sterilization, the medium was inoculated with a loopful of *Streptomyces anulatus* 3533-SV4 strain (FERM BP-6460). The inoculated culture in the test tube was then subjected to shake-culturing at 27° C. on a reciprocal shaker for 2 days.

Then, a production medium (pH 7.2) containing 2.0% glycerin, 1.0% molasses, 0.5% casein, 0.1% polypeptone and 0.4% calcium carbonate was distributed into conical flasks of 500 ml capacity, 100 ml per flask, and after sterilization (121° C., 15 min.), the above seed culture was added at a ratio of 2% (v/v) to each flask. The culture in the flasks were subjected to shake-culturing at 27° C. on a rotary shaker for 3 days (220 rounds per minute, 7 cm throw).

Subsequently, each of three jar fermentors (Marubishi Bioengineering Co., Ltd.) of 50 liter capacity was charged with 30,000 ml of the above production medium. To the jar fermentors were added an antifoaming agents (15 ml Disfoam (CC-118, Nippon Oil and Fats Co., Ltd.), 15 ml Shin-Etsu Silicone (KM-68-2F Shin-Etsu Chemical Co., Ltd.) and 15 ml Salad Oil (Ajinomoto Co., Inc.)), and after sterilization (120° C., 20 min.), the above seed culture was added at a ratio of 2% (v/v) to each jar fermentor. The culture in the jar fermentors was subjected to culturing at 27° C. for 3 days (aerobic spinner: 400 rpm (agitation), 30 l/min (aeration)).

(b) Separation Process

The culture broth obtained by the above procedure was harvested in an amount of 84.0 l, and centrifuged to separate cell pellets. After discarding supernatant fluid, the cell pellets were subjected to two-hour extraction with acetone (10.0 l) under frequent stirring. The extract was separated by filtration and the extraction and separation was then repeated with an additional volume of acetone of 5.0 l. Those acetone extracts were combined, and then distilled and concentrated to the final volume of 2 l. The solvent was distilled off under reduced pressure until acetone and water had been completely evaporated. The obtained oily residue was dissolved in 450 ml methanol and after being filtered, evaporated to dryness under reduced pressure.

(c) Isolation and Purification Process

The obtained oily residue was dissolved in 400 ml of a mixed solvent comprising chloroform and methanol (20:1) (v/v). The solution was applied to a silica gel column (Wakogel C-200 (particle size 75–150 μm), 6 cm I.D.×45 cm) and eluted with 5 l of a chloroform/methanol mixed solvent prepared as above. Fractions containing an active substance were eluted with a chloroform/methanol solvent (10:1) (v/v). The fractions containing an active substance were collected and evaporated to dryness under reduced pressure. The crude purified substance was applied to a silica gel column (particle size 75–150 μm), 3.6 cm I.D.×30 cm) and eluted with a mixture of chloroform/methanol/29% ammonia aqueous solution (700:100:1) (v/v/v).

An eluate containing an active substance was collected and evaporated to dryness. The residue was dissolved in 10 ml of the above mobile phase, and then applied to High Performance Liquid Chromatography using PEGASIL ODS column (Senshu Scientific Co., 20 mm I.D.×250 mm) (mobile phase: acetonitrile/trifluoroacetic acid/water (70:0.1:30, v/v/v), flow rate: 10.0 ml/min, 254 nm (detected in 0.5 mm UV cell)). The extract in an amount of 0.8 ml was injected each time. Fractions containing Substance GM-95 were collected and were evaporated to dryness under reduced pressure.

The residue was suspended in 10% methanol/water, and then applied to PEGASIL ODS column (Senshu Scientific Co., 1.0 cm I.D.×3 cm). After the column was washed with 10% methanol/water, elution was carried out with 70% methanol/water. The eluate was distilled off under reduced pressure to provide 3.2 mg of Substance GM-95.

Fractions containing Substance GM-95 in each stage of purification were detected by High Performance Liquid Chromatography using PEGASIL ODS column (Senshu Scientific Co., 4.6 mm I.D.×250 mm) (mobile phase: acetonitrile/trifluoroacetic acid/water (70:0.1:30, v/v/v)), flow rate: 1.0 ml/min).

Physicochemical properties of Substance GM-95 are as follows.
1) Molecular formula: When measured by high-resolution fast atomic bombardment mass spectrometry, the measured value of (M+H)$^+$ of 583.0790 is shown, and the molecular formula which corresponds to the value is $C_{26}H_{15}N_8O_7S$.
2) Molecular weight: When measured by fast atomic bombardment mass spectrometry, the measured value of 582.0712 is shown.
3) Melting point: 138–143° C. (decomposition)
4) Specific rotation: $[\alpha]_D^{20}=-9.38°$, determined at the concentration of C=0.129 g/100 ml (methanol).
5) Ultraviolet absorption spectrum: shown in FIG. 1.

The measurement was conducted in methanol (in a 7.39 μM solution). The maximum absorption was at the wavelength of 259.5 nm and the absorbance at the wavelength was 0.288. A molar absorption coefficient (δ) was 38982.
6) Infrared absorption spectrum (FT-IR): shown in FIG. 2. vmax (cm$^{-1}$):

3421, 3147, 2958, 2923, 2854, 1733, 1670, 1650, 1544, 1496, 1438, 1392, 1351, 1315, 1267, 1199, 1174, 1118, 1087, 1058, 1033, 975, 943, 929, 914, 883, 798
7) Solubilities in solvents
    Insoluble in water and in acetone.
    Soluble in a mixture of chloroform:methanol=1:1
8) Color of the substance: white yellowish powders
9) Nuclear magnetic resonance spectrum The chemical shifts of the 500 MHz $^1$H-NMR spectrum (FIG. 3) and the 125 MHz $^{13}$C-NMR spectrum (FIG. 4) measured in the solution of a mixture of neuterated chloroform:deuterated methanol=1:1 at 25° C. are shown below.

TABLE 4

| Position of carbon | $^{13}$C-NMR | $^1$H-NMR |
|---|---|---|
| 1 | 162.5 | |
| 2 | 150.5 | |
| 3 | 125.1 | |
| 4 | 155.4 | |
| 5 | 149.6 | |
| 6 | 126.0 | |
| 7 | 157.3 | |
| 8 | 137.8 | 8.17 (s, 1 H) |
| 9 | 130.4 | |
| 10 | 156.8 | |
| 11 | 138.8 | 8.24 (s, 1 H) |
| 12 | 130.7 | |
| 13 | 156.2 | |
| 14 | 141.2 | 8.00 (s, 1 H) |
| 15 | 136.7 | |
| 16 | 156.6 | |
| 17 | 139.4 | 8.28 (s, 1 H) |
| 18 | 130.9 | |
| 19 | 156.6 | |
| 20 | 138.1 | 8.18 (s, 1 H) |
| 21 | 130.4 | |
| 22 | 160.0 | |
| 23 | 38.7 | 3.8 (m, 1 H), 3.46 (m, 1 H) |
| 24 | 73.2 | 6.19 (br s, 1 H) |
| 25 | 11.5 | 2.47 (s, 3 H) |
| 26 | 11.5 | 2.64 (s, 3 H) |

(10) Retention time (Rt) in high performance liquid chromatography (HPLC):

A peak was detected at a time of 6.1 min. upon analysis under the following conditions.

Analytical Conditions:

Column: PEGASIL ODS (4.6 mm I.D.×250 mm, Senshu Scientific Co.)

Mobile phase: acetonitrile/trifluoroacetic acid/water (70:0.1:30, v/v/v)

Flow rate: 1 ml/min.

Detection: 254 nm

According to the above physicochemical data, the structure of Substance GM-95 was identified as below.

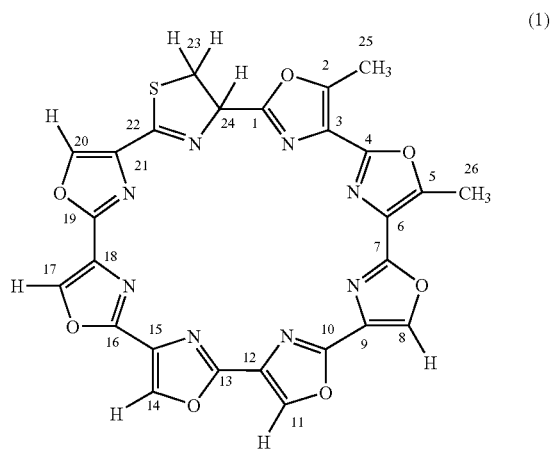

(1)

Pharmacological Test (Antitumor Effects)

Tumor cells described in Table 5 were suspended in RPMI1640 medium containing 10% fetal calf serum, plated into culture plates (38 mm) at the density of in 2×10$^3$ cells each, and cultured in 37° C., 5% $CO_2$ incubator overnight. Subsequently, experimental agents (the compound of the invention and 5-fluorouracil) diluted to various concentrations using RPMI1640 medium containing 10% fetal calf serum were added to each plate, and further cultured for 72 hours. After the cell culture was completed, those cells were fixed with 25% glutalaldehyde for 15 minutes and washed with water three times. After that, the cells were stained with 0.05% crystal violet diluted in 20% methanol aqueous solution, washed with water three times and then dried. The crystal violet were extracted with 100 μl of 0.05M sodium dihydrogenphosphate/ethanol (1/1(v/v)), their absorbance at 540 nm were determined by an automatic spectroscope. "IC$_{50}$" was defined as the concentration required for a 50% reduction in growth compared to the control absorbance. The results are as follows.

TABLE 5

Concentrations for 50% growth inhibition of various tumor cells (IC$_{50}$ μM)

| cell strain (derivation) | the compound of the invention | 5-fluorouracil |
|---|---|---|
| OVCAR-3 (human ovarian cancer) | 3.41 | 0.37 |
| PC-3 (human prostate cancer) | 8.82 | 5.7 |
| SKOV-3 (human ovarian cancer) | 3.73 | 7.84 |
| MCF-7 (human breast cancer) | 7.73 | 1.12 |
| ZR75-1 (human breast cancer) | 4.04 | 3.63 |
| PAN-3 (human pancreatic cancer) | 7.09 | 8.82 |
| KM12C-SM (human colon cancer) | 3.74 | 1.32 |
| A375SM (human melanoma) | 7.04 | 2.89 |
| TMK-1 (human gastric cancer) | 3.75 | 0.33 |
| HT-29 (human colon cancer) | 7.1 | 2.1 |
| DLD-1 (human colon cancer) | 6.2 | 5.5 |
| Renca (mouse renal cancer) | 0.97 | 0.58 |

The compound of the present invention could have inhibited in vitro growth of various tumor cells.

Pharmacological Test (Telomerase-inhibiting Effects)

The compound of the invention was subjected to the examination of telomerase-inhibiting activity using cell extracts containing telomerase according to the conventional manner, to provide the concentration for inhibiting telomerase activity by 50% (IC$_{50}$) in cell extracts. The compound of the invention was proved to have a IC$_{50}$ value of 50 nM, and therefore to have extremely strong telomerase-inhibiting activity.

Telomerase hardly exists in normal cells, but widely exists in various malignant tumors (found in 85% or more of all the malignant tumors including those originating from the region of skin, breast, lung, stomach, pancreatic, ovarian, neck, uterus, kidney, bladder, colon and prostate, in a central nervous system (CNS), in retina and in a blood cell system). The compound of the present invention inhibits the activity of said enzyme, suggesting that it is useful as an antitumor agent having a wide spectrum of usage.

Formulation Example 1. Capsules

| Substance GM-95 | 10 mg |
|---|---|
| Lactose | 50 mg |
| Corn starch | 47 mg |
| Crystalline cellulose | 50 mg |
| Talc | 2 mg |
| Magnesium stearate | 1 mg |
| Per capsule | 160 mg |

According to the above recipe, capsules were manufactured in the conventional manner.

Formulation Example 2. Injection

| Substance GM-95 | 5 mg |
|---|---|
| Distilled water for injection | suitable amount |
| Per ampule | 5 ml |

According to the above recipe, an injection was manufactured in the conventional manner.

Formulation Example 3. Suppositories

| Substance GM-95 | 20 mg |
|---|---|
| Witepsol W-35 (trademark of Dynamit Nobel Co., Ltd.) | 1380 mg |
| Per suppository | 1400 mg |

According to the above recipe, suppositories were manufactured in the conventional manner.

INDUSTRIAL APPLICABILITY

The substance GM-95 of the present invention has the excellent antitumor effect and is useful as a therapeutic drug for malignant tumors. Further, the substance GM-95-producing microorganism is useful because it is capable of producing Substance GM-95 having the excellent antitumor effect.

The invention claimed is:

1. A microorganism, isolated from a biologically pure culture, which (1) belongs to the genus *Streptomyces*, (2) possesses all of the morphological and physiological characteristics of *Streptomyces anulatus* 3533-SV4 strain, and (3) produces a compound represented by the following formula (1)

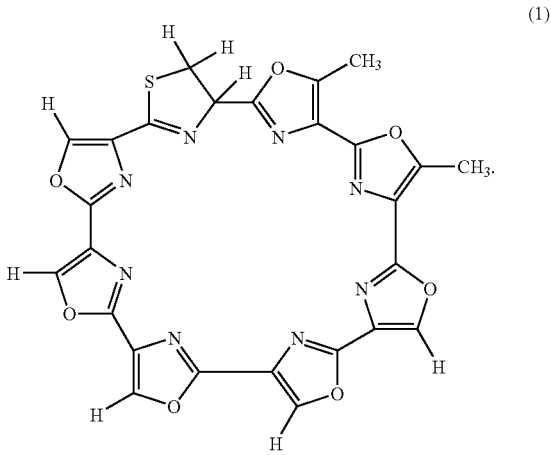

2. The microorganism according to claim 1, which is the *Streptomyces anulatus* 3533-SV4 strain deposited with the National Institute of Bioscience and Human-Technology Agency of Industrial Science and Technology, Japan under the accession number of FERM BP-6460.

3. A biologically pure culture of a microorganism which (1) belongs to the genus *Streptomyces*, (2) possesses all of the morphological and physiological characteristics of *Streptomyces anulatus* 3533-SV4 strain, and (3) produces a compound represented by the following formula (1)

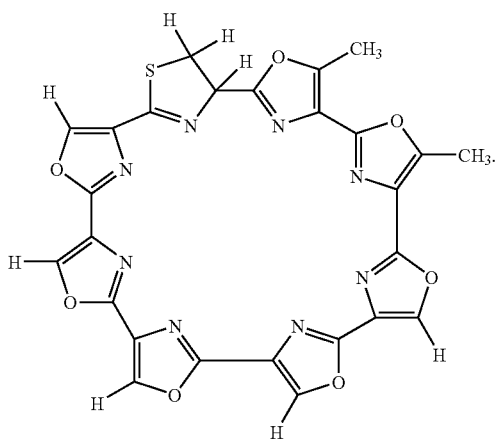
(1)

4. The biologically pure culture of the microorganism according to claim 3, which is the *Streptomyces anulatus* 3533-SV4 strain deposited with the National Institute of Bioscience and Human-Technology Agency of Industrial Science and Technology, Japan under the accession number of FERM BP-6460.

5. A process for producing a compound represented by the following formula (1),

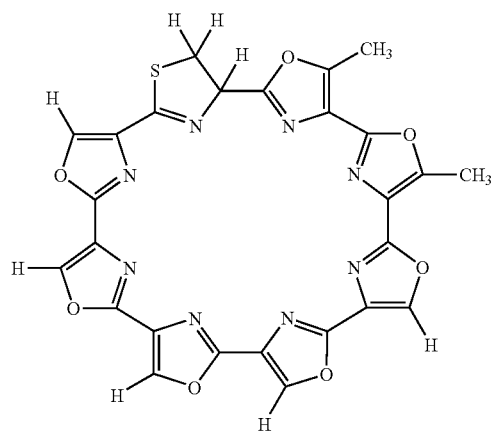
(1)

which method comprises cultivating the microorganism according to claim 1, in a culture medium under conditions to produce the compound, and isolating the compound from the culture medium.

6. The process according to claim 5, wherein the microorganism is the *Streptomyces anulatus* 3533-SV4 strain deposited with the National Institute of Bioscience and Human-Technology Agency of Industrial Science and Technology, Japan under the accession number of FERM BP-6460.

7. A process for producing a compound represented by the following formula (1),

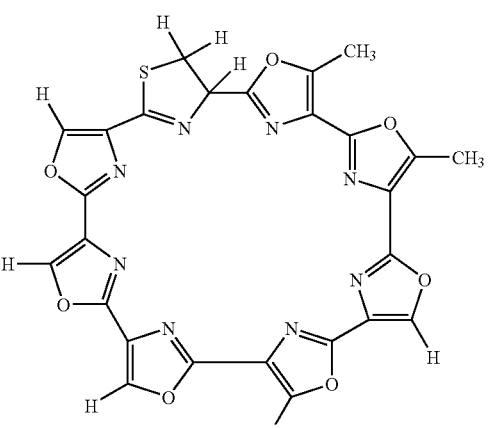
(1)

which method comprises cultivating the biologically pure culture of the microorganism according to claim 3, in a culture medium under conditions to produce the compound, and isolating the compound from the culture medium.

8. The process according to claim 7, wherein the microorganism is the *Streptomyces anulatus* 3533-SV4 strain deposited with the National Institute of Bioscience and Human-Technology Agency of Industrial Science and Technology, Japan under the accession number of FERM BP-6460.

* * * * *

UNITED STATES PATENT AND TRADEMARK OFFICE
CERTIFICATE OF CORRECTION

| | | |
|---|---|---|
| PATENT NO. | : 7,192,763 B2 | Page 1 of 1 |
| APPLICATION NO. | : 10/401589 | |
| DATED | : March 20, 2007 | |
| INVENTOR(S) | : Haruo Seto et al. | |

It is certified that error appears in the above-identified patent and that said Letters Patent is hereby corrected as shown below:

Title Page:
Item (63) should be read as follows:
-- Division of application No. 09/806,475, filed as application No. PCT/JP99/05806 on Oct. 20, 1999, now Pat. No. 6,613,759 --.

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,192,763 B2 |
| APPLICATION NO. | : 10/401589 |
| DATED | : March 20, 2007 |
| INVENTOR(S) | : Haruo Seto et al. |

It is certified that error appears in the above-identified patent and that said Letters Patent is hereby corrected as shown below:

<u>Title Page:</u>
Item (30) should be read as follows:
-- October 23, 1998 (JP).......................................................10-302634 --

Signed and Sealed this

Sixth Day of November, 2007

JON W. DUDAS
*Director of the United States Patent and Trademark Office*